United States Patent
Sun et al.

(10) Patent No.: US 10,022,448 B2
(45) Date of Patent: *Jul. 17, 2018

(54) TOPICAL GEL COMPOSITIONS INCLUDING POLYCAPROLACTONE POLYMER AND METHODS FOR ENHANCING THE TOPICAL APPLICATION OF A BENEFIT AGENT

(71) Applicant: Johnson & Johnson Consumer Inc., Skillman, NJ (US)

(72) Inventors: Ying Sun, Belle Mead, NJ (US); Anna Gosiewska, Skillman, NJ (US); Dennis D. Jamiolkowski, Long Valley, NJ (US); Jeffrey M. Wu, Princeton, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/696,662

(22) Filed: Sep. 6, 2017

(65) Prior Publication Data

US 2017/0360941 A1 Dec. 21, 2017

Related U.S. Application Data

(60) Continuation of application No. 15/346,113, filed on Nov. 8, 2016, now Pat. No. 9,782,485, which is a division of application No. 14/138,338, filed on Dec. 23, 2013, now abandoned.

(51) Int. Cl.

| | |
|---|---|
| *A01N 43/54* | (2006.01) |
| *A61K 31/505* | (2006.01) |
| *A61K 47/34* | (2017.01) |
| *A61K 31/506* | (2006.01) |
| *A61K 8/34* | (2006.01) |
| *A61K 31/192* | (2006.01) |
| *A61Q 7/00* | (2006.01) |
| *A61K 8/49* | (2006.01) |
| *A61K 8/04* | (2006.01) |
| *A61K 9/00* | (2006.01) |
| *A61K 8/85* | (2006.01) |
| *A61Q 19/00* | (2006.01) |
| *A61K 47/10* | (2017.01) |
| *A61Q 19/08* | (2006.01) |
| *A61Q 19/02* | (2006.01) |

(52) U.S. Cl.
CPC ............ *A61K 47/34* (2013.01); *A61K 8/042* (2013.01); *A61K 8/34* (2013.01); *A61K 8/345* (2013.01); *A61K 8/4953* (2013.01); *A61K 8/85* (2013.01); *A61K 9/0014* (2013.01); *A61K 31/192* (2013.01); *A61K 31/506* (2013.01); *A61K 47/10* (2013.01); *A61Q 7/00* (2013.01); *A61Q 19/00* (2013.01); *A61K 2800/591* (2013.01); *A61Q 19/02* (2013.01); *A61Q 19/08* (2013.01)

(58) Field of Classification Search
None
See application file for complete search history.

(56) References Cited

U.S. PATENT DOCUMENTS

| | | |
|---|---|---|
| 6,419,913 B1 | 7/2002 | Niemiec et al. |
| 6,432,415 B1 | 8/2002 | Osborne et al. |
| 8,454,945 B2 | 6/2013 | McCook |
| 8,470,833 B2 | 6/2013 | Hu et al. |
| 8,470,880 B2 | 6/2013 | Hu et al. |
| 2002/0006418 A1 | 1/2002 | Kung et al. |
| 2005/0163811 A1* | 7/2005 | Lee ............... A61K 8/362 424/400 |
| 2007/0092574 A1 | 4/2007 | Cook |
| 2008/0206171 A1 | 8/2008 | Gueniche |
| 2013/0324567 A1 | 12/2013 | Liu |
| 2014/0135349 A1 | 5/2014 | Kalem |
| 2015/0174254 A1 | 6/2015 | Sun et al. |
| 2015/0216986 A1* | 8/2015 | Pohlmann ...... A61K 9/0014 514/275 |
| 2017/0049681 A1 | 2/2017 | Sun et al. |

FOREIGN PATENT DOCUMENTS

| | | |
|---|---|---|
| EP | 1269972 A | 1/2003 |
| WO | WO 2005/000258 A | 1/2005 |
| WO | WO 2008/041245 A | 4/2008 |

OTHER PUBLICATIONS

H.-I Chang et al., "Delivery of the antibiotic gentamicin sulphate from precipitation cast matrices of polycaprolactone", Journal of Controlled Release 110 (2006) 414-421.
International Search Report for corresponding PCT Application No. PCT/US2014/070574 dated Mar. 10, 2015.
Shim et al., "Transdermal delivery of minoxidil with block copolymer nanoparticles," Journal of Controlled Release 97 (2004) 477-484.
Woodruff, et al., "The return of a forgotten polymer—Polycaprolactone in the 21$^{st}$ century", Prog Polym Sci (2010), doi: 10.1016/j.progpolymsci.2010.04.002.

* cited by examiner

*Primary Examiner* — Jared Barsky

(57) ABSTRACT

A composition comprising: a benefit agent; at least one polymer including a polycaprolactone polymer; at least one lower alcohol; and at least one co-solvent; and a method for enhancing topical delivery of a benefit agent is disclosed.

2 Claims, No Drawings

TOPICAL GEL COMPOSITIONS INCLUDING POLYCAPROLACTONE POLYMER AND METHODS FOR ENHANCING THE TOPICAL APPLICATION OF A BENEFIT AGENT

CROSS-REFERENCE TO RELATED APPLICATIONS

This application is a continuation of U.S. patent application Ser. No. 15/346,113 filed Nov. 8, 2016, which is a divisional of U.S. patent application Ser. No. 14/138,338 filed Dec. 23, 2013, the disclosures of which are hereby incorporated by reference in their entirety.

The present invention relates to compositions and methods for enhancing the topical application of a benefit agent. The compositions may be gels including a benefit agent, at least one polymer including a polycaprolactone polymer, at least one lower alcohol, and at least one co-solvent. The compositions are useful in topically applied personal care applications.

BACKGROUND OF THE INVENTION

Liquid compositions for delivering benefit agents are well known. Typical formulations include solutions, emulsions, suspensions and gels. The viscosity may vary based on intended area for application, intended use (leave on or rinse off), or consumer preference. Liquids are typically easy to dispense and spread out. There is a continuing need for improved liquid compositions.

There is also a need for compositions that improve skin penetration of benefit agents. U.S. Pat. No. 6,419,913 teaches micellar compositions that enhance skin penetration. Although effective, these compositions can be difficult to manufacture and the cost of the products are relatively high.

Polycaprolactone (PCL) is a polymer used for implantable/injectable drug delivery systems for medical implants (M. A. Woodruff & D. W. Hutmacher, The return of a forgotten polymer—Polycaprolactone in the 21st century, Progress in Polymer Science, Vol. 35 (10), 2010, pages 1217-1256), or as a carrier to encapsulate or immoblize a drug for sustained release purpose (H. I. Chang, et. al, Delivery of the antibiotic gentamicin sulphate from precipitation cast matrices of polycaprolactone, J. Controlled Release, Vol. 110, 2:10, 2006, pages 414-421).

However, PCL has not been shown as a skin permeation enhancing component in a topical composition to enhance a topical applied drug to penetrate into the intact skin.

Applicants have now discovered novel compositions and a method of enhancing the topical application of benefit agents. The compositions include gels including a benefit agent, at least one polymer including a polycaprolactone polymer, at least one lower alcohol, at least one co-solvent and water. The compositions can be used in cosmetic, skin care, wound care, dermatologic, and other personal care products, as well as in other applications and industries.

SUMMARY OF THE INVENTION

The invention provides a topical composition comprising at least one polycaprolactone polymer, at least one lower alcohol, and at least one co-solvent. The invention also provides a personal care composition comprising the above composition and a method for enhancing the topical application of a benefit agent.

DETAILED DESCRIPTION OF THE INVENTION

As used herein, unless otherwise specified, all percentages are by weight based on the total weight of composition referred to.

The disclosures of all patents and published applications referred to herein are incorporated by reference in their entirety.

As used herein, "benefit agent" is a compound (e.g., a synthetic compound or a compound isolated from a natural source) that has a cosmetic or therapeutic effect on tissue (e.g., a material capable of exerting a biological effect on the human body) such as therapeutic drugs or cosmetic agents. Examples of benefit agents include small molecules, peptides, proteins, nucleic acid materials, and nutrients such as minerals and extracts. The amount of the benefit agent used will depend on the benefit agent and/or the intended use of the end product. Benefit agents may be liquid, solid, or semi-solid.

As used herein, "pharmaceutically acceptable," "cosmetically acceptable," or "dermatologically acceptable" means suitable for use in contact with tissues (e.g., the skin, hair, mucosa, epithelium or the like) without undue toxicity, incompatibility, instability, irritation, or allergic response.

As used herein, "safe and effective amount" means an amount sufficient to provide a desired benefit at a desired level, but low enough to avoid serious undesirable side effects. The safe and effective amount of the ingredient or composition will vary with the area being treated, the age of the end user, the duration and nature of the treatment, the specific ingredient or composition employed, the particular carrier utilized, and like factors.

As used herein, the term "treating" or "treatment" means the alleviation or elimination of symptoms, cure, prevention, or inhibition of a disease or medical condition, or improvement of tissue growth/healing or cosmetic conditions such as reducing appearance of skin wrinkles/fine lines, under-eye bags, cellulites, skin marks/hyperpigmentation or uneven tone.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

The polymers used to make the compositions of the present invention include a polycaprolactone polymer. The polycaprolactone polymer can be selected from the group consisting of hydroxypolycaprolactone; polycaprolactone diol ($\alpha$, $\omega$-dihydroxy poly($\varepsilon$-caprolactone)); polycaprolactone triol; $\alpha$, $\omega$-dihydroxy oligo($\varepsilon$-caprolactone); $\alpha$-carboxy, $\omega$-hydroxy poly($\varepsilon$-caprolactone) $\alpha$, $\omega$-dicarboxy poly($\varepsilon$-caprolactone) and mixtures thereof.

Polycaprolactone [poly($\varepsilon$-caprolactone)] can be made by a ring opening polymerization of the lactone monomer $\varepsilon$-caprolactone using an alcohol, such as dodecanol, as an initiator and a catalyst, such as stannous octoate. The resulting polymer contains an alkyl functionality at one end and an alcohol functionality at the other. If however the initiator is chosen to be a diol, both ends of the formed polymer will be hydroxy terminated. Polycaprolactone made by ring-opening polymerization using either a monol or a diol as initiator will be linear in molecular structure.

The relative molar amount of the initiator present during the polymerization controls the molecular weight of the formed polymer. The higher the relative amount of initiator, the lower the molecular weight of the formed polymer.

It is possible to produce polycaprolactone without hydroxyl groups at the chain ends. This could be accomplished by capping the chain ends, using for instance succinic anhydride to result in a carboxy end group instead of a hydroxyl end group, as part of the synthesis of the resin.

α, ω-dicarboxy poly(ε-caprolactone) can be made by using a diol such as diethylene glycol as the polymerization initiator followed by reaction with a cyclic anhydride such as diglycolic anhydride or succinic anhydride; an alternate route to this polymer is using a hydroxy acid such as glycolic acid as the polymerization initiator followed by reaction with a cyclic anhydride such as diglycolic anhydride or succinic anhydride.

Additionally the polycaprolactone polymer can be a hydroxylated polycaprolactone polymer. The polymer may have between 1 and 3 hydroxyl substitutions. The polymer can be a hydroxypolycaprolactone, polycaprolactone diol; polycaprolactone triol and mixtures thereof. The polycaprolactone triol can be made by using a triol initiator, such as glycerol, or trimethylolpropane (TMP); polycaprolactone triol does not possess a linear structure but is a branched polymer.

Compositions of the present invention preferably include a polycaprolactone diol polymer. The polycaprolactone diol polymer molecular weight may range from about 500 Dalton to about 50,000 Dalton, for example from about 1,000 Dalton to about 5,000 Dalton, or from about 1,200 Dalton to about 2,500 Dalton, or from about 1,250 Dalton to about 2,000 Dalton. The amount of the polymer is sufficient to form a gel and may range from about 0.05% to about 20%, or from 0.1% to about 20%, or from about 0.5% to about 10%, or from about 1% to about 10%, or from about 1% to about 5% by weight based on the total weight of the composition. The methods for measuring the molecular weight are those known in the art.

The topical compositions of the present invention also include at least one lower alcohol. Suitable alcohols include ethyl alcohol, n-propyl alcohol, isopropyl alcohol, n-butyl alcohol, isobutyl alcohol, amyl alcohol, benzyl alcohol, octyldocanol, hexyldecanol, butyloctanol, and mixtures thereof. The amount of alcohol may range from about 2% to about 90% or from about 5% to about 80%, or from about 5% to about 40%, or from about 10% to about 30%, or from about 15% to about 25% by weight based on the total weight of the composition.

Compositions according to the present invention also include a co-solvent. Suitable co-solvents include one or more polyols. Such polyols include, but are not limited to glycerol (glycerin), polyglycerols, glycols, polyglycols, and mixtures thereof.

Examples of polyglycerols include, but are not limited to diglycerol (diglycerin), triglycerol (polyglcerin-3 or polyglycerol-3), tetraglycerol (polyglycerin-4 or polyglycerol-4), other polyglycerols (polycerol-n, where n>4), and mixtures thereof.

Examples of glycols include, but are not limited to propylene glycol, ethylene glycol, butylene glycol and its isomers (e.g., 1,2-butanediol, 1,3-butanediol, 1,4-butanediol and 2,3-butanediol), pentylene glycol, hexylene glycol and its isomers, propanediol, dipropylene glycol, ethoxydiglycol, methylpropanediol, isopentyldiol, and mixtures thereof.

Examples of polyglycols include, but are not limited to, polyethylene glycol of various molecular weights, namely, molecular weights ranging from 300 g/mol to 10,000,000 g/mol, (e.g., PEG-200, PEG-400, PEG-1000, PEG-2000 PEG-4000, PEG-6000), polypropylene glycol (PPG) of various molecular weights, and mixtures thereof.

The amount of co-solvent may range from about 1% to about 50%, or from about 5% to about 50%, or from about 10% to about 40% or from about 10% to about 20% by weight based on the total weight of the composition.

The compositions of the present invention may also include water. The amount of water may range from about 20% to about 80%, or from about 30% to about 60%, or from about 40% to about 50% by weight based on the total weight of the composition.

In one embodiment, the composition may further comprise at least one hydrophilic polymer, e.g., natural or synthetic hydrophilic polymers. Such hydrophilic polymer may be soluble or partially soluble in the gel. Suitable hydrophilic polymers include, but are not limited to, homo- and copolymers of vinyl pyrrolidone (e.g., PVP, or PVP/PVA copolymer), homo- or copolymers of vinyl alcohol (e.g., polyvinyl alcohol or PVA), polyacrylamide, homo- or copolymers of acrylic and/or methacrylic acids, and salts and esters thereof (e.g., CARBOPO/CARBOMER 934, 940, 941, 980, 1342, and 1382, and ULTREZ 10 and 21), cellulosic polymers (e.g., hydroxymethylcellulose, hydroxyethyl cellulose, carboxy methyl cellulose, carboxy ethyl cellulose), polyurethanes, starch and its derivatives, and synthetic and natural gums (e.g., gum arabic or xanthan gum). Preferred hydrophilic polymers are acrylate polymers and copolymers, particularly polyacrylate neutralized by anhydrous neutralizers.

If used, the amount of the hydrophilic polymer is usually up to about 10%, or equal to or less than about 5%, or equal to or less than about 3%, or equal to or less than about 2%, by weight of the composition.

In general, the topical composition may contain any additional ingredients (e.g., benefit agents or formulation excipients) soluble or dispersible in the gel or its components. Pharmaceutically or cosmetically acceptable benefit agents or excipients, such as extracts of plants or minerals, natural or synthetic compounds of small molecular weight or polymers, acids or bases (particularly week acids or bases) for acidity adjustment, buffers, chelators, antioxidants, thickeners or gelling agents can be used.

The topical composition has great versatility in application, and can be used in many consumer and medical products for human and animal use such topical compositions (such as creams, lotions, gels, shampoos, cleansers, powders patches, bandages, and masks for application to the skin or mucosal membranes), garments (such as undergarments, underwear, bras, shirts, pants, pantyhose, socks, head caps, facial masks, gloves, and mittens), linens (such as towels, pillow covers or cases and bed sheets), sanitizing products for household and clinical settings, microcides for plants, and devices (such as toothbrushes, dental flosses, periodontal implants or inserts, orthodontic braces, joint wraps/supports, buccal patches, ocular inserts or implants such as contact lenses, nasal implants or inserts, and contact lens cleaning products, wound dressings, diapers, sanitary napkins, wipes, tampons, rectal and vaginal suppositories, and in coatings or embedded surfaces on medical devices and other surfaces where antimicrobial or other beneficial effects are desired).

The topical composition may be any form suitable for application to the skin or an animal or human. The forms may include gels, solutions, lotions, ointments, mousses, foams, sprays, aerosols, shampoos, creams, pastes or other topical composition forms known in the art.

When applied to the skin the topical composition is formulated to be readily absorbed into the skin with minimal amount of rubbing. The composition provides an easy to apply topical composition that can be used to delivery numerous benefit agents to the skin.

The topical composition can be incorporated onto fibers, nonwovens, hydrocolloids, adhesives, films, polymers, and other substrates. In one embodiment, the composition is in contact with a tissue interface. Methods of applying the composition on substrates include spray coating, co-extrusion, and adhesive spraying.

The topical composition may contain a wide range of benefit agents used for various applications as described in the sections below.

The composition may be administered topically, locally (via buccal, nasal, rectal or vaginal route) to a subject (e.g., a human) in need of treatment for a condition or disease, or to otherwise provide a therapeutic effect. Such therapeutic effects include, but are not limited to: antimicrobial effects (e.g., antibacterial, antifungal, antiviral, and anti-parasitic effects); anti-inflammation effects including effects in the superficial or deep tissues (e.g., reduce or elimination of soft tissue edema or redness); elimination or reduction of pain, itch or other sensory discomfort; regeneration or healing enhancement of hard tissues (e.g., enhancing growth rate of the nail or regrowth of hair loss due to alopecia) or increase soft tissue volume (e.g., increasing collagen or elastin in the skin or lips); increasing adipocyte metabolism or improving body appearance (e.g., effects on body contour or shape, and cellulite reduction); and increasing circulation of blood or lymphocytes.

In one embodiment, the composition further contains a safe and effective amount of a benefit agent, for example, from about 0.001% to about 20%, or from about 0.01% to about 10%, or from about 1% to about 5% by weight of the composition of the benefit agent.

In one embodiment, the invention provides a topical composition containing the composition that is suitable for administering to mammalian skin, such as human skin. In one embodiment, such topical composition contains a safe and effective amount of (i) the composition, and (ii) a cosmetically- or pharmaceutically-acceptable carrier.

The topical compositions may be made into a wide variety of products that include but are not limited to leave-on products (such as lotions, creams, gels, sticks, sprays, and ointments), skin cleansing products (such as liquid washes, solid bars, and wipes), hair products (such as shampoos, conditioners, sprays, and mousses), shaving creams, film-forming products (such as masks), make-up (such as foundations, eye liners, and eye shadows), deodorant and antiperspirant compositions, and the like. These product types may contain any of several cosmetically- or pharmaceutically-acceptable carrier forms including, but not limited to solutions, suspensions, emulsions such as microemulsions and nanoemulsions, gels, and solids carrier forms. Other product forms can be formulated by those of ordinary skill in the art.

In one embodiment, the topical composition is used for the treatment of skin conditions. Examples of such skin conditions include, but are not limited to acne (e.g., blackheads and whiteheads), rosacea, nodule-cystic, and other microbial infections of the skin; visible signs of skin aging (e.g., wrinkles, sagging, sallowness, and age-spots); loose or lax skin, folliculitis and pseudo-folliculitis barbae; excess sebum (e.g., for sebum reduction or oily/shining skin appearance inhibition or control); pigmentation (e.g., for reduction of hyperpigmentation such as freckles, melasma, actinic and senile lentigines, age-spots, post-inflammatory hypermelanosis, Becker's naevus, and facial melanosis or enhancing the pigmentation of light skin); excess hair growth (e.g., skin on the leg), or insufficient hair growth (e.g., on the scalp); dermatitis (e.g., atopic, contact, or seborrheic dermatitis), dark circles under the eye, stretch marks, cellulite, excessive sweating (e.g., hyperhidrosis), and/or psoriasis.

(a) Topical Anti-Acne/Anti-Rosacea Compositions

In one embodiment, the topical composition also contains an anti-acne and/or anti-rosacea active agent. Examples of anti-acne and anti-rosacea agents include, but are not limited to: retinoids such as tretinoin, isotretinoin, motretinide, adapalene, tazarotene, azelaic acid, and retinol; salicylic acid; resorcinol; sulfacetamide; urea; antibiotics such as tetracycline, clindamycin, metronidazole, and erythromycin; anti-inflammatory agents such as corticosteroids (e.g., hydrocortisone), ibuprofen, naproxen, and hetprofen; and imidazoles such as ketoconazole and elubiol; and salts and prodrugs thereof. Other examples of anti-acne active agents include essential oils, alpha-bisabolol, dipotassium glycyrrhizinate, camphor, β-glucan, allantoin, feverfew, flavonoids such as soy isoflavones, saw palmetto, chelating agents such as EDTA, lipase inhibitors such as silver and copper ions, hydrolyzed vegetable proteins, inorganic ions of chloride, iodide, fluoride, and their nonionic derivatives chlorine, iodine, fluorine, and synthetic phospholipids and natural phospholipids such as ARLASILK™ phospholipids CDM, SV, EFA, PLN, and GLA (commercially available from Uniqema, ICI Group of Companies, Wilton, UK).

(b) Topical Anti-Aging Compositions

In one embodiment, the topical composition also contains an anti-aging agent. Examples of suitable anti-aging agents include, but are not limited to; retinoids; dimethylaminoethanol (DMAE), copper containing peptides, vitamins such as vitamin E, vitamin A (retinol and its derivatives, e.g., retinyl palmitate), vitamin C (ascorbic acid and its derivative, e.g., Ascorbic Acid 2-Glucoside/AA2G), and vitamin B (e.g., niacinamide, niacin) and vitamin salts or derivatives such as ascorbic acid di-glucoside and vitamin E acetate or palmitate; alpha hydroxy acids and their precursors such as glycolic acid, citric acid, lactic acid, malic acid, mandelic acid, ascorbic acid, alpha-hydroxybutyric acid, alpha-hydroxyisobutyric acid, alpha-hydroxyisocaproic acid, atrolactic acid, alpha-hydroxyisovaleric acid, ethyl pyruvate, galacturonic acid, glucoheptonic acid, glucoheptono 1,4-lactone, gluconic acid, gluconolactone, glucuronic acid, glucuronolactone, isopropyl pyruvate, methyl pyruvate, mucic acid, pyruvic acid, saccharic acid, saccharic acid 1,4-lactone, tartaric acid, and tartronic acid; beta hydroxy acids such as beta-hydroxybutyric acid, beta-phenyl-lactic acid, and beta-phenylpyruvic acid; tetrahydroxypropyl ethylenediamine, N,N,N',N'-Tetrakis(2-hydroxypropyl)ethylenediamine (THPED); and botanical extracts such as green tea, soy, milk thistle, algae, aloe, *angelica*, bitter orange, coffee, goldthread, grapefruit, hoellen, honeysuckle, Job's tears, *lithospermum*, mulberry, peony, puerarua, nice, and safflower; and salts and prodrugs thereof.

(c) Topical Depigmentation Compositions

In one embodiment, the topical composition contains a depigmentation agent. Examples of suitable depigmentation agents include, but are not limited to: soy extract; soy isoflavones; retinoids such as retinol; kojic acid; kojic dipalmitate; hydroquinone; arbutin; transexamic acid; vitamins such as niacinamide, niacin and vitamin C (ascorbic acid and AA2G; azelaic acid; linolenic acid and linoleic acid; placertia; licorice; and extracts such as chamomile, grape seeds and green tea; and salts and prodrugs thereof.

(d) Topical Antipsoriatic Compositions

In one embodiment, the topical composition contains an antipsoriatic active agent. Examples of antipsoriatic active agents (e.g., for seborrheic dermatitis treatment) include, but are not limited to, corticosteroids (e.g., betamethasone dipropionate, betamethasone valerate, clobetasol propionate, diflorasone diacetate, halobetasol propionate, triamcinonide, dexamethasone, fluocinonide, fluocinolone acetonide, halcinonide, triamcinolone acetate, hydrocortisone, hydrocortisone verlerate, hydrocortisone butyrate, aclometasone dipropionte, flurandrenolide, mometasone furoate, methylprednisolone acetate), methotrexate, cyclosporine, calcipotriene, anthraline, shale oil and derivatives thereof, elubiol, ketoconazole, coal tar, salicylic acid, zinc pyrithione, selenium sulfide, hydrocortisone, sulfur, menthol, and pramoxine hydrochloride, and salts and prodrugs thereof (e) Other Topical Ingredients In one embodiment, the topical composition contains a plant extract as a benefit agent. Examples of plant extracts include, but are not limited to, feverfew, soy, *glycine soja*, oatmeal, what, aloe vera, cranberry, witch-hazel, *alnus, arnica, artemisia capillaris*, asiasarum root, birch, *calendula*, chamomile, *cnidium*, comfrey, fennel, galla rhois, hawthorn, *houttuynia, hypericum*, jujube, kiwi, licorice, *magnolia*, olive, peppermint, *philodendron, salvia*, sasa albo-marginata, natural isoflavonoids, soy isoflavones, and natural essential oils.

In one embodiment, the topical composition contains one or more buffering agents such as citrate buffer, phosphate buffer, lactate buffer, gluconate buffer, or gelling agent, thickener, or polymer.

In one embodiment, the composition or product contains a fragrance effective for reducing stress, calming, and/or affecting sleep such as lavender and chamomile.

The composition can be incorporated into compositions for the treatment of periodontal disease with actives such as, but not limited to minocycline.

In one embodiment, the composition is incorporated into wound dressings or bandages to provide healing enhancement or scar prevention. Wounds or lesions that may be treated include, but are not limited to acute wounds as well as chronic wounds including diabetic ulcer, venus ulcer, and pressure sores.

In one embodiment, the wound dressing or bandage contains a benefit agent commonly used as for topical wound and scar treatment, such as antibiotics, anti-microbials, wound healing enhancing agents, antifungal drugs, anti-psoriatic drugs, and anti-inflammatory agents.

Examples of antifungal drugs include but are not limited to miconazole, econazole, ketoconazole, sertaconazole, itraconazole, fluconazole, voriconazole, clioquinol, bifoconazole, terconazole, butoconazole, tioconazole, oxiconazole, sulconazole, saperconazole, clotrimazole, undecylenic acid, haloprogin, butenafine, tolnaftate, nystatin, ciclopirox olamine, terbinafine, amorolfine, naftifine, elubiol, griseofulvin, and their pharmaceutically acceptable salts and prodrugs. In one embodiment, the antifungal drug is an azole, an allylamine, or a mixture thereof.

Examples of antibiotics (or antiseptics) include but are not limited to mupirocin, neomycin sulfate bacitracin, polymyxin B, 1-ofloxacin, tetracyclines (chlortetracycline hydrochloride, oxytetracycline-10 hydrochloride and tetrachcycline hydrochloride), clindamycin phosphate, gentamicin sulfate, metronidazole, hexylresorcinol, methylbenzethonium chloride, phenol, quaternary ammonium compounds, tea tree oil, and their pharmaceutically acceptable salts and prodrugs.

Examples of antimicrobials include but are not limited to salts of chlorhexidine, such as Iodopropynyl butylcarbamate, diazolidinyl urea, chlorhexidene digluconate, chlorhexidene acetate, chlorhexidene isethionate, and chlorhexidene hydrochloride. Other cationic antimicrobials may also be used, such as benzalkonium chloride, benzethonium chloride, triclocarbon, polyhexamethylene biguanide, cetylpyridium chloride, methyl and benzethonium chloride. Other antimicrobials include, but are not limited to: halogenated phenolic compounds, such as 2,4,4',-trichloro-2-hydroxy diphenyl ether (Triclosan); parachlorometa xylenol (PCMX); and short chain alcohols, such as ethanol, propanol, and the like. In one embodiment, the alcohol is at a low concentration (e.g., less than about 10% by weight of the carrier, such as less than 5% by weight of the carrier) so that it does not cause undue drying of the barrier membrane.

Examples of anti-viral agents for viral infections such as herpes and hepatitis, include, but are not limited to, imiquimod and its derivatives, podofilox, podophyllin, interferon alpha, acyclovir, famcyclovir, valcyclovir, reticulos and cidofovir, and salts and prodrugs thereof.

Examples of anti-inflammatory agents include, but are not limited to, suitable steroidal anti-inflammatory agents such as corticosteroids such as hydrocortisone, hydroxyltriamcinolone alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, and salts are prodrugs thereof. In one embodiment, the steroidal anti-inflammatory for use in the present invention is hydrocortisone. A second class of anti-inflammatory agents which is useful in the compositions of the present invention includes the nonsteroidal anti-inflammatory agents.

Examples of wound healing enhancing agents include recombinant human platelet-derived growth factor (PDGF) and other growth factors, ketanserin, iloprost, prostaglandin E1 and hyaluronic acid, scar reducing agents such as mannose-6-phosphate, analgesic agents, anesthetics, hair growth enhancing agents such as minoxadil, hair growth retarding agents such as eflornithine hydrochloride, antihypertensives, drugs to treat coronary artery diseases, anticancer agents, endocrine and metabolic medication, neurologic medications, medication for cessation of chemical additions, motion sickness, protein and peptide drugs.

In one embodiment, the composition is used, with or without other antifungal active agents, to treat or prevent fungal infections (e.g., dermatophytes such as *trichophyton mentagrophytes*), including, but not limited to, onychomycosis, sporotrichosis, tinea unguium, tinea pedis (athlete's foot), tinea cruris (jock itch), tinea corporis (ringworm), tinea capitis, tinea versicolor, and *candida* yeast infection-related diseases (e.g., *candida albicans*) such as diaper rash, oral thrushm, cutaneous and vaginal candidiasis, genital rashes, *Malassezia furfur* infection-related diseases such as Pityriasis versicolor, Pityriasis folliculitis, seborrhoeic dermatitis, and dandruff.

In another embodiment, the composition is used, with or without other antibacterial active agents, to treat and prevent bacterial infections, including, but not limited to, acne, cellulitis, erysipelas, impetigo, folliculitis, and furuncles and carbuncles, as well as acute wounds and chronic wounds (venous ulcers, diabetic ulcers and pressure ulcers).

In another embodiment, the composition is used, with or without other antiviral active agents, to treat and prevent viral infections of the skin and mucosa, including, but not limited to, molluscum contagiosum, warts, herpes simplex virus infections such as cold sores, kanker sores and genital herpes.

In another embodiment, the composition is used, with or without other antiparasitic active agents, to treat and prevent parasitic infections, including, but not limited to, hookworm infection, lice, scabies, sea bathers' eruption and swimmer's itch.

In one embodiment, the composition is administered to treat ear infections (such as those caused by *streptococcus pneumoniae*), rhinitis and/or sinusitis (such as caused by *Haemophilus influenzae, Moraxella catarrhalis, Staphylococcus aureus* and *Streptococcus pneumoniae*), and strep throat (such as caused by *Streptococcus pyogenes*).

The composition can also be used to stimulate nail growth, enhance nail strength, and reduce nail infection or discoloration. The composition can be incorporated into compositions for the treatment of onychomychosis with actives such as, but not limited to miconazole, econazole, ketoconazole, sertaconazole, itraconazole, fluconazole, voricoriazole, clioquinol, bifoconazole, terconazole, butoconazole, tioconazole, oxiconazole, sulconazole, saperconazole, clotrimazole, undecylenic acid, haloprogin, butenafine, tolnaftate, nystatin, ciclopirox olamine, terbinafine, amorolfine, naftifine, elubiol, griseofulvin, and their pharmaceutically acceptable salts and prodrugs. The composition can be incorporated into compositions for improving the look and feel of nails with ingredients such as, but not limited to: biotin, calcium panthotenate, tocopheryl acetate, panthenol, phytantriol, cholecalciferol, calcium chloride, Aloe Barbadensis (Leaf Juice), silk protein, soy protein, hydrogen peroxide, carbamide peroxide, green tea extract, acetylcysteine and cysteine.

The composition can be combined with certain active agents for the growth of hair, or improving or thickening of hair of the scalp, eye brow or eye lash, may be used to treat hair conditions topically. Compositions containing drug(s) and/or active agents to stimulate hair growth and/or prevent hair loss and/or regrow hair, including, but not limited to, minoxidil, finasteride, or lumigan may be employed.

The composition has a unique advantage over conventional hair treatment compositions due to its excellent flowability. For example, the gel can easily reach the scalp through thinned hair in the case of alopecia treatment.

The composition may contain certain analgesic active agents and as such may be prepared for topical treatment of pain, such as pain at or from the back, shoulder, joints, muscle sore/pain, menstrual cramps, or pain from cold sore or canker sore. Benefit agents to relieve pain include, but are not limited to, NonSteroidal Anti-Inflammatory Drugs (NSAIDs) such as ibuprofen, naproxen, salicylic acid, ketoprofen, and diclofenac and their pharmaceutically acceptable salts thereof. Other topical analgesic active agents for treating pain and itch include, but are not limited to, methyl salicylate, menthol, trolamine salicylate, capsaicin, lidocaine, benzocaine, pramoxine hydrochloride, and hydrocortisone.

EXAMPLES

Examples are set forth below to further illustrate the nature of the invention and the manner of carrying it out. However, the invention should not be considered as being limited to the details thereof.

Example 1

Polycaprolactone diol was purchased from Polysciences, Inc. (Warrington, Pa.). One sample was 1,250 Daltons; the other sample was molecular weight 2,000 Daltons.

A gel was made with the ingredients in Table 1 and following the procedure below:

TABLE 1

| Chemical Name | Formula A | Formula B | Formula C |
|---|---|---|---|
| Ethyl Alcohol | 20.00 | 20.00 | 20.00 |
| Pentylene Glycol | 4.00 | 4.00 | 4.00 |
| Glycerin | 12.00 | 12.00 | 12.00 |
| Lactic Acid | 3.20 | 3.20 | 3.20 |
| Minoxidil | 5.00 | 5.00 | 5.00 |
| Butylated Hydroxytoluene | 0.10 | 0.10 | 0.10 |
| Water | 52.20 | 49.2 | 49.2 |
| Steareth-10 | 1.50 | 1.5 | 1.5 |
| Steareth-2 | 2.00 | 2.00 | 2.00 |
| Polycaprolactone diol (Mwt = 1250) | 0.0 | 3.0 | 0.0 |
| Polycaprolactone diol (Mwt = 2000) | 0.0 | 0.0 | 3.0 |
| Total | 100.00 | 100.00 | 100.00 |

Step 1—20 parts of ethyl alcohol, 4 parts of pentylene glycol, 12 parts of glycerin, 3.2 parts of lactic acid, 0.10 parts of butylated hydroxytoluene, and 5 parts of minoxidil were added to a glass container and mixed until the solution is clear at room temperature.

Step 2—In a separate glass container, 49.2 parts of water, 3 parts of polycaprolactone diol (if present), 1.5 parts of steareth-10, and 2 parts of steareth-2 were added. The mixture was heated to about 75° C. to melt the contents and a mixer was used to mix it for 5-10 minutes until completely uniform.

After the water phase in step 2 cooled back to room temperature the mix from step #1 was added and, using a high speed homogenizer, the mixture was homogenized for about 5 minutes.

Example 2—In Vitro Skin Permeation of 5% Minoxidil Compositions Through Human Cadaver Skin A skin penetration study evaluated the penetration of minoxidil into different skin layers for the inventive samples (Formulas B and C) prepared as disclosed in Example 1 vs. a test sample without the PCL polymer (Formula A). A well-known Franz diffusion cell method (as taught in US20020006418 A1, which is hereby incorporated by reference) was used. Franz cells had a diameter of 0.5 cm$^2$ and a volume of liquid receptor of 5 ml. A magnetic stirrer bar was added in the donor compartment. The liquid receptor was filled with Phosphate-buffered saline (PBS) solution. Air bubbles in the donor compartment were removed. The system was thermostated at 37° C. above a magnetic stirrer to ensure the homogeneity of the liquid receptor during the experiment. A cadaver skin sample from a commercial tissue bank (Ohio Valley Tissue and Skin Center, Cincinnati, Ohio, dermatomed to approximately 0.4 mm) was cut to fit the glass diffusion cell and mounted skin on the Franz cell. A test sample of 20 microliters was applied on the skin surface. Samples were collected from the receptor compartment at scheduled time points of 0, 1, 3 and 6 hours. At the end of the study the skin surface was washed with a cotton swab soaked with PBS (total four times). The cotton swabs were collected for drug analysis later. After washing, D-square tape (CuDerm Corp., Dallas, Tex.) was used to separate the stratum corneum from epidermis by pressing the tape onto the skin surface and remove it. The same process of tape-stripping was repeated four more times (total 5 times). All the tapes were collected for each skin samples for drug extraction later. Epidermis layer was separated from dermis tissue by pressing the epidermis side of the skin onto a 60° C. hot plate for 1 minute, then peeling off the epidermis layer from the dermis tissue with a pair of forceps. Extraction was performed using methanol as extraction solvent from the collected tapes (drug on and in the stratum corneum), epidermis (drug penetrated into the epidermis tissue) and dermis (drug penetrated into the dermis tissue). Samples collected from the receptor compartment and from the extraction processes, as well as from the washing process were analyzed for minoxidil levels with a Waters High-performance liquid chromatography (HPLC) system with the procedure listed below. The results are shown in Tables 2 and 3. The final average minoxidil levels in different skin layers are reported in micrograms (μg) for 3 different replicates. A minoxidil mass balance study was also conducted and the % of recovery of minoxidil was equal or better than 94% for both the control (Formula A) and the inventive formulations (Formulas B and C).

TABLE 2

| | Time (hr) | Formula A (microgram) | Formula B (microgram) | Ratio Formula B/Formula A |
|---|---|---|---|---|
| Cumulative Minoxidil in Receptor | 0 | 0 | 0 | 0 |
| | 3 | 14.7 | 22.3 | 1.52 |
| | 6 | 37.3 | 48.8 | 1.31 |
| Dermis | 6 | 10.2 | 10.4 | 1.02 |
| Epidermis | 6 | 12.7 | 21.6 | 1.70 |
| Tapes | 6 | 5.2 | 12.4 | — |
| Wash | 6 | 770 | 749 | — |
| % Recovered | 6 | 95% | 96% | — |

TABLE 3

| | Time (hr) | Formula A (microgram) | Formula C (microgram) | Ratio between Formula C vs. Formula A |
|---|---|---|---|---|
| Cumulative Minoxidil in Receptor | 0 | 0 | 0 | 0 |
| | 3 | 14.7 | 22.6 | 1.54 |
| | 6 | 37.3 | 50.3 | 1.35 |
| Dermis | 6 | 10.2 | 15.0 | 1.47 |
| Epidermis | 6 | 12.7 | 21.3 | 1.68 |
| Tapes | 6 | 5.2 | 13.5 | — |
| Wash | 6 | 770 | 764 | — |
| % Recovered | 6 | 95% | 94% | — |

Because the target tissue for topical minoxidil delivery is the hair follicles (hair "roots") residing deep in the dermis, only minoxidil that penetrated into and across the dermis layer could reach the hair follicles, and therefore, are of practical significance. The cumulative minoxidil in the receptor is the measurement of the total minoxidil that penetrated across all the layers of the skin including the dermis. It is surprising that the gel compositions of the present invention have enhanced minoxidil delivery deep into and across the human skin in comparison to the control formulation with the same drug concentration, as demonstrated by the results in Tables 2 and 3. This is an unexpected finding since all three formulas have the same solvents at the same amounts.

HPLC Procedure for Minoxidil Quantification

A HPLC System (Waters Alliance® HPLC system) was used to measure minoxidil with UV absorption response at 286 nm. A Luna 5 μM C18(2) 250×4.6-mm HPLC column (Phenomenex) was used to separate the minoxidil analyte from other impurities in the extract samples for surface rinse, stripped tape, epidermis, dermis, and receptor solution. The mobile phase was an isocratic 80% (70:29:1 water/methanol/acetic acid—pH 3.3):20% methanol.

Example 3

Polycaprolactone diol was purchased from Polysciences, Inc. (Warrington, Pa.). One sample was 1,250 Daltons; the other sample was molecular weight 2,000 Daltons.

Gels were made with the ingredients in Table 4 and following the procedure below:

TABLE 4

| Chemical Name | Formula D | Formula E |
|---|---|---|
| Ethyl Alcohol, USP (95%) | 20.00 | 20.00 |
| Pentylene Glycol | 4.00 | 4.00 |
| Glycerin | 12.00 | 12.00 |
| Sodium Hydroxide | 1.00 | 1.00 |
| Ibuprofen | 5.00 | 5.00 |
| Butylated Hydroxytoluene | 0.10 | 0.10 |
| Water | 51.40 | 51.40 |
| Steareth-10 | 1.50 | 1.50 |
| Steareth-2 | 2.00 | 2.00 |
| Polycaprolactone diol (Mwt = 1250) | 1.0 | 0.0 |
| Polycaprolactone diol (Mwt = 2000) | 0.0 | 1.0 |
| Sodium Hydroxide (20% in water) | Adjust the aqueous phase to pH6 | Adjust the aqueous phase to pH6 |

TABLE 4-continued

| Chemical Name | Formula D | Formula E |
|---|---|---|
| Water | Add To 100 | Add To 100 |
| Hydroxypropylcellulose (KLUCEL, HF Pharm) | 1.00 | 1.00 |
| Total | 101.00 | 101.00 |

Step 1—20 parts of ethyl alcohol, 4 parts of pentylene glycol, 12 parts of glycerin, 0.10 parts of butylated hydroxytoluene, 5 parts of ibuprofen, and 30 parts of purified water were added to a glass container. The pH was adjusted to pH 6 using 20% NaOH aqueous solution at room temperature. The amount of NaOH and water added was recorded.

Step 2—1 part of polycaprolactone diol, 1.5 parts of steareth-10, and 2 parts of steareth-2 were added in a separate glass container. The remaining parts of purified water were added until the total amount of the composition was equal to 100 parts. The mixture was heated to about 75° C. to melt the contents, and use a mixer was used to mix it for 5-10 minutes until completely uniform.

After the water phase in step 2 cooled back to room temperature the mix from step 1 was added and a high speed homogenizer was used to homogenize the mixture for about 5 minutes. 1 part of hydroxypropylcellulose was added and mixed until a uniform translucent gel was formed. The pH was measured to confirm the final pH of the composition.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

We Claim:

1. A method for enhancing the topical application of a benefit agent which comprises topically administering to a human or animal a gel composition comprising
   minoxidil in an amount from about 1% to about 5% by weight of the composition;
   polycaprolactone diol in an amount from about 1% to about 10% by weight of the composition;
   ethyl alcohol in an amount from about 5% to about 40% by weight of the composition;
   lactic acid and
   glycerin in an amount from about 5% to about 20% by weight of the composition.

2. The method according to claim 1 wherein
   the polycaprolactone diol is in an amount from about 1% to about 5% by weight of the composition;
   the ethyl alcohol is in an amount from about 10% to about 30% by weight of the composition;
   the lactic acid is in an amount about 3.2% by weight of the composition;
   and
   the glycerin is in an amount from about 10% to about 20% by weight of the composition.

* * * * *